United States Patent [19]
Dickerson et al.

[11] Patent Number: 5,458,789
[45] Date of Patent: * Oct. 17, 1995

[54] REMOVAL OF ORGANICS FROM AQUEOUS WASTE STREAMS

[76] Inventors: J. Rodney Dickerson, 105 Young Dr., Lafayette, La. 70506; Paul C. Broussard, Sr., P.O. Box 53446, Lafayette, La. 70505

[*] Notice: The portion of the term of this patent subsequent to Mar. 14, 2012 has been disclaimed.

[21] Appl. No.: 166,514

[22] Filed: Dec. 14, 1993

Related U.S. Application Data

[63] Continuation-in-part of Ser. No. 166,645, Dec. 12, 1993, Pat. No. 5,397,480, which is a continuation-in-part of Ser. No. 856,100, Mar. 23, 1993, abandoned.

[51] Int. Cl.$^6$ .................................................. C02F 1/74
[52] U.S. Cl. .................. 210/750; 210/752; 210/758; 210/765; 95/263; 95/265; 261/116; 261/DIG. 42
[58] Field of Search .......................... 210/928, 760, 210/758, 757, 908, 192, 199, 206, 218, 220, 221.2, 259, 752, 750, 765; 95/263, 264, 265; 261/116, DIG. 42

[56] References Cited

U.S. PATENT DOCUMENTS

| | | | |
|---|---|---|---|
| 804,589 | 11/1905 | Enrico | 261/116 |
| 2,447,123 | 8/1948 | Jones | 261/116 |
| 2,970,821 | 2/1961 | Axt | 210/192 |
| 3,445,001 | 5/1969 | LaRaus | 210/192 |
| 3,674,216 | 7/1972 | Blair | 241/277 |
| 3,761,065 | 9/1973 | Rich et al. | 261/DIG. 54 |
| 3,772,188 | 11/1973 | Edwards | 210/197 |
| 4,104,166 | 8/1978 | LaRaus | 210/259 |
| 4,351,732 | 9/1982 | Psaras et al. | 210/689 |
| 4,696,739 | 9/1987 | Pedneault | 210/192 |
| 4,898,679 | 2/1990 | Siegel et al. | 210/760 |
| 5,004,537 | 4/1991 | Brown | 210/192 |
| 5,053,140 | 10/1991 | Hurst | 210/704 |
| 5,116,574 | 5/1992 | Pearson | 422/3 |
| 5,122,165 | 6/1992 | Wang et al. | 95/263 |
| 5,173,257 | 12/1992 | Pearson | 210/760 |
| 5,273,664 | 12/1993 | Schulz | 210/192 |
| 5,281,254 | 1/1994 | Birbara et al. | 95/44 |
| 5,397,480 | 3/1995 | Dickerson | 210/752 |

*Primary Examiner*—Cynthia L. Nessler
*Attorney, Agent, or Firm*—William David Kiesel; Robert C. Tucker

[57] ABSTRACT

Apparatus and process for removing relatively low levels of components, particularly organic components found in an aqueous stream in one or more stripping zones located in a process unit. An eductor means extending into each stripping zone is used to provide micro-fine gas bubbles which will dissolve the volatile components and carry them from the aqueous stream.

10 Claims, 2 Drawing Sheets

REMOVAL OF ORGANICS FROM AQUEOUS WASTE STREAMS

CROSS-REFERENCE TO RELATED APPLICATIONS

This is a continuation-in-part of U.S. patent application No. 08/166,645, filed together with this application, on Dec. 13, 1993, now U.S. Pat. No. 5,397,480 which is a continuation-in-part of U.S. patent application Ser. No. 07/856,100 filed on Mar. 23, 1993, now abandoned.

FIELD OF THE INVENTION

The present invention relates to a process for removing relatively low levels of organic components from an aqueous stream in one or more stripping zones. An eductor means is used in each stripping zone for providing micro-fine bubbles, in which the volatile components will dissolve and are carried from the aqueous stream.

BACKGROUND OF THE INVENTION

A substantial number of aqueous streams must be treated to meet governmental laws and regulations to certify them for drinking purposes or for release into the environment. Non-limiting examples of such aqueous streams include: those emanating from municipal water supplies; those waste water streams resulting from various chemical, petrochemical, and refining processes; and, those resulting from various other industries such as the pulp and paper industry. Contaminated ground water streams must also be treated depending on their intended use. Such aqueous streams typically contain one or more impurity, such as suspended matter, organic components, etc.

One type of aqueous stream which has proven difficult to treat in a cost effective manner is an aqueous stream containing relatively low levels of organic components, typically volatile organic components. Such streams are often found in petroleum refineries and chemical plants wherein water is often initially present, or subsequently found in processes for producing various organic chemicals and products therefrom.

Various conventional techniques are presently used to remove relatively low levels of organic contaminants from aqueous streams. One leading technique involves air stripping. Air stripping techniques typically involve the use of packed, or bubble tray, columns wherein the contaminated aqueous stream is passed counter-current to a flow of air. Organic moieties pass from the aqueous liquid phase to the gaseous phase owing to the difference in concentration of organics in the two phases. That is, the organic constituents pass from the more concentrated aqueous phase to the less concentrated gaseous phase. The stripped organics are eventually released to the atmosphere with the vented air.

The use of columns has the disadvantage of being prone to fouling owing to deposits which result during the evaporation of water. Undesirable amounts of biomass also have a tendency to form in the columns. Consequently, such conventional techniques are subject to a relatively rapid decline of performance, thereby resulting in a substantial amount of down-time needed to clean the columns. Typically, two or more columns are used so that one or more columns are still in operation while one is being cleaned. The need for these additional column(s) increases the capital investment requirements of the process.

Another conventional technique consists of bubbling air directly into the contaminated aqueous stream by use of diffusers or bubblers. Although such a technique is effective for removing organics from the stream, no more than trace amounts, typically less than about 10 ppm, or even less, of the organic constituents can be present for the process to be effective. A source of compressed air is also needed, thereby increasing the capital investment and operating costs.

Other conventional techniques for removing organic constituents from aqueous streams include adsorption onto a solid adsorbent material, such as activated carbon. This technique suffers from the need to regenerate the adsorbent by removing the adsorbed organic material. This is typically done by subjecting the adsorbent to steam, which is then condensed to form a condensate stream composed of an aqueous phase and an organic phase. After gross physical separation of the organic phase from the aqueous phase, an aqueous stream is left with a relatively low, but still undesirable, level of organic constituents. These organic constituents may or may not be soluble in the aqueous stream.

Another conventional technique involves the destruction of organic constituents in the liquid phase by use of ultraviolet light; or by use of an oxidant, such as ozone, hydrogen peroxide, or both. Such techniques typically require substantial capital investment and are relatively expensive to operate and maintain.

Distillation is also an alternative technique, but is also capital intensive and costly to operate. Further, distillation is not effective for separating organic molecules which form an azeotrope with water.

Therefore, there still remains a substantial need in the art for more efficient and effective processes for removing relatively low, but still undesirable levels of organic constituents from aqueous streams.

SUMMARY OF THE INVENTION

In accordance with the present invention, there is provided a process for stripping relatively low levels of organic components from an aqueous stream in a process unit comprised of one or more serially connected stripping zones, wherein the aqueous stream is fed into the lead stripping zone and is serially passed through the stripping zones to the tail stripping zone where it exits the process unit, wherein in each stripping zone the aqueous stream is contacted with a flow of micro-fine gas bubbles which are supplied by one or more eductor means, which eductor means are driven by the recycled aqueous stream.

In a preferred embodiment of the present invention, the organic contaminants are selected from the group consisting of benzene, toluene, xylenes, and methyl ethyl ketone.

In another preferred embodiment of the present invention, inorganic acids, such as carbonic acid, are also removed.

In yet another preferred embodiment of the present invention, at least three stripping zones are present.

PREFERRED EMBODIMENTS OF THE INVENTION

The present invention can be practiced on any aqueous stream which contains relatively low levels of organic contaminants. It is preferred that the level of organic contaminants not be more than about 0.5 wt. %, preferably not more than about 0.1 wt. %. Further, the organics may be any organic compound which is a liquid at the temperature and pressure of the aqueous stream. Generally, the aqueous stream will be found at a temperature of about 5° C. to 40° C. and at atmospheric pressures. The types of organic contaminants which will typically be found in industrial waste water streams include organic solvents, such as benzene, toluene, xylene, and methyl ethyl ketone. It is to be understood that inorganic contaminants, such as inorganic acids, particularly carbonic acid, may also be present in the aqueous streams and may also be removed by the practice of the present invention.

Aqueous streams which are generally found with relatively low levels of organics are those streams which are a by-product of the chemical and petroleum industry. A typical aqueous stream containing such organic contaminants would be an aqueous stream which is generated during the manufacture of various polymeric products. For example, one or more organic contaminants, such as organic solvents, can be released during manufacture, particularly during the curing, of polymer products, and typically end up in a waste water stream. Such contaminants are typically removed by passing the contaminated stream through a bed of solid adsorbent material, such as activated carbon. The contaminants are adsorbed onto the adsorbent, which can then be regenerated by stripping the adsorbent of the contaminant material. Steam is the typical desorbent material. The steam is then condensed, thereby forming an aqueous/organic condensate stream. After a gross physical separation of an organic phase from an aqueous phase, the stream will usually still contain organic moieties, primarily in the form of water soluble, or miscible, compounds.

A typical condensate aqueous stream from the curing of polymeric products, particularly elastomeric products, will contain up to about 200 ppm of toluene and up to about 900 ppm of methyl ethyl ketone. The stream may also contain enough carbonic acid, which is formed during the steam stripping step, to lower the pH of the aqueous stream to about 4. Such a stream cannot be air stripped in conventional equipment because of the large volume of air that would be required. Also, the low pH of such a stream creates handling and corrosion problems for conventional air stripping units.

Figure 1:
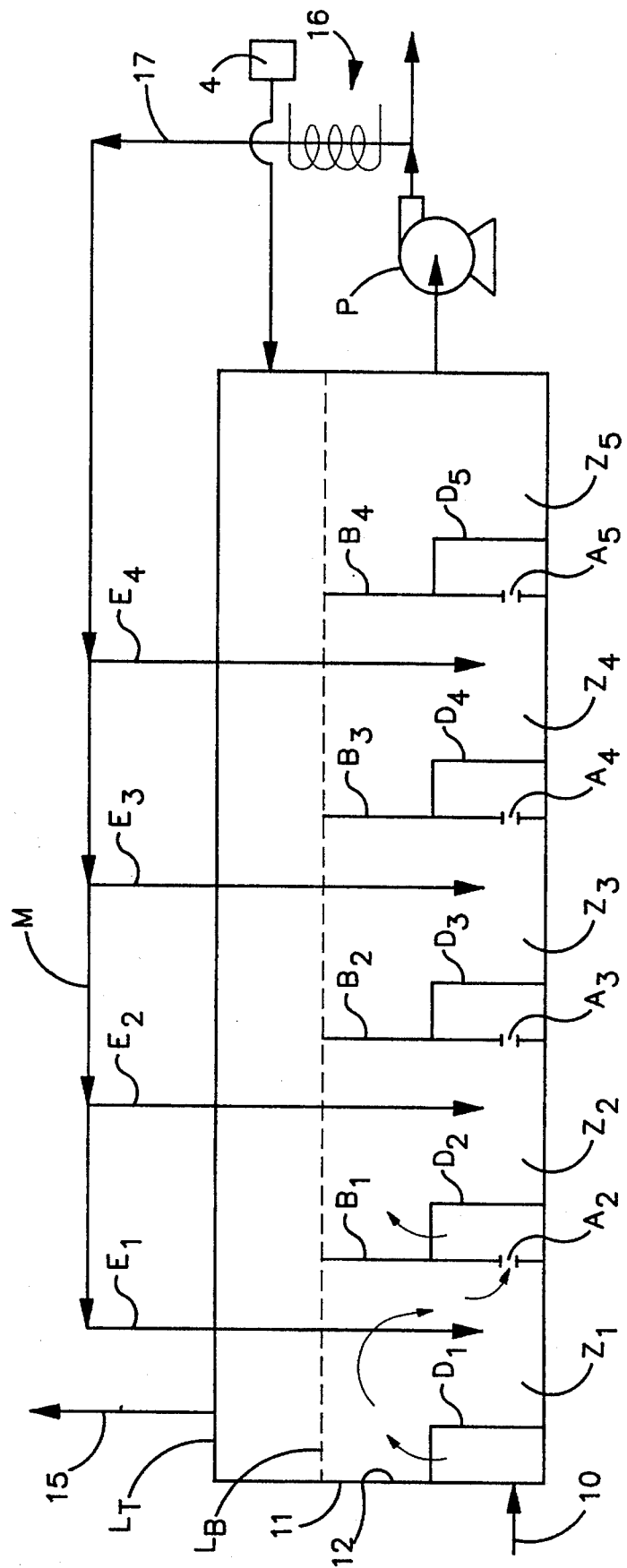
FIG. 1 is a simplified schematic flow diagram of a preferred embodiment of the present invention showing a process unit containing four stripping zones. Each stripping zone contains an eductor means disposed therein and each eductor means is driven by recycle liquid.
Figure 4:
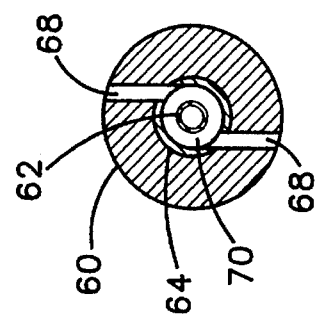
FIG. 4 is a cross-sectional view in a horizontal plane indicated by line 4—4 in FIG. 2. This Figure shows a preferred arrangement of inlets to the eductor means for an enhanced gas flow.

FIG. 1 hereof is a simplified depiction of a preferred process unit 1, in which the present invention can be practiced. The process unit 1 in this Figure is a single fully enclosed vessel, which is divided into five serially connected zones $Z_1$ to $Z_5$, each in fluid communication with its next upstream and downstream zone, and each separated from one another by use of a baffle means $B_1$ to $B_4$. The baffle means extends from the bottom of the process unit 1 to a point below the roof $L_T$ of the process unit 1, so that a headspace is created. That is, an air space remains between the top of the liquid which is defined by the top of the baffles $L_B$, and the roof $L_T$ of the process unit 1. Typically, the baffles will extend from about 50% to 90%, preferably from about 70% to 80% to the top of the process unit 1. Each baffle means will contain an aperture A at its bottom section to allow the aqueous stream to be passed from one zone to the next downstream zone. Each baffle means $B_1$ to $B_4$ will also contain a diverter means $D_2$ to $D_5$ on its downstream surface. Another diverter means $D_1$ is attached to the interior surface 12 of the upstream end-wall 11 of the process unit 1. The diverter means $D_2$ to $D_5$ are each preferably an open ended elongated box type of a structure which is substantially vertically secured to the downstream surface of its corresponding baffle means $B_1$ to $B_4$ and spaced at a predetermined distance from the downstream side of its corresponding aperture $A_3$ to $A_5$ and the downstream side wall 13 of process unit 1. This allows the flow of the aqueous stream, which passes through each aperture, to be directed upward toward the surface of the liquid in each stripping zone. The apertures at the bottom of the baffles are preferably horizontally staggered from one baffle to another. That is, the aperture of the next downstream baffle is preferably on the opposite side (left or right) relative to the aperture of the next upstream baffle. The first four zones are stripping zones and the last zone is an accumulation zone for de-gassing purposes, in the process unit of FIG. 1 hereof.

Each stripping zone contains an eductor means $E_1$ to $E_4$, submerged therein, which supplies a stripping gas, such as air, carbon dioxide, nitrogen, methane, or mixtures thereof, in the form of micro-fine bubbles, for stripping the organics. The preferred stripping gas is air.

The number of stripping zones employed will depend on such things as the type of organic contaminants to be removed, their concentration, and the desired level of removal.

Turning again to FIG. 1, the present invention is practiced by feeding the aqueous stream containing the organic contaminants to zone $Z_1$ via line 10 through an inlet aperture (not shown) in the upstream end-wall of the treatment unit. The stream enters the zone and is directed by diverter means $D_1$ toward the level $L_B$ of liquid in the zone, which will typically not be higher than the top of baffles, $B_1$ to $B_4$. All of the baffles are preferably at the same height. The stream flows to the next downstream zone by passing through the aperture $A_2$ at the bottom of the next downstream baffle means, $B_1$. The stream is diverted upward by diverter means $D_2$. This sequence is continued until the stream flows into last zone $Z_5$, where it is accumulated and de-gassed.

In each of the four stripping zones, $Z_1$ to $Z_4$, the stream is contacted with micro-fine bubbles of stripping gas which are introduced into the liquid in each zone by one or more eductor means. It is preferred that the micro-fine bubbles be introduced deep into each stripping zone to ensure that the micro-fine bubbles travel through as much of each stripping zone as possible.

Figure 3:
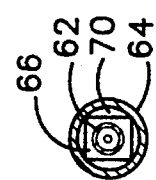
FIG. 3 is a cross-sectional view in a horizontal plane indicated by line 3—3 in FIG. 2.
Figure 2:
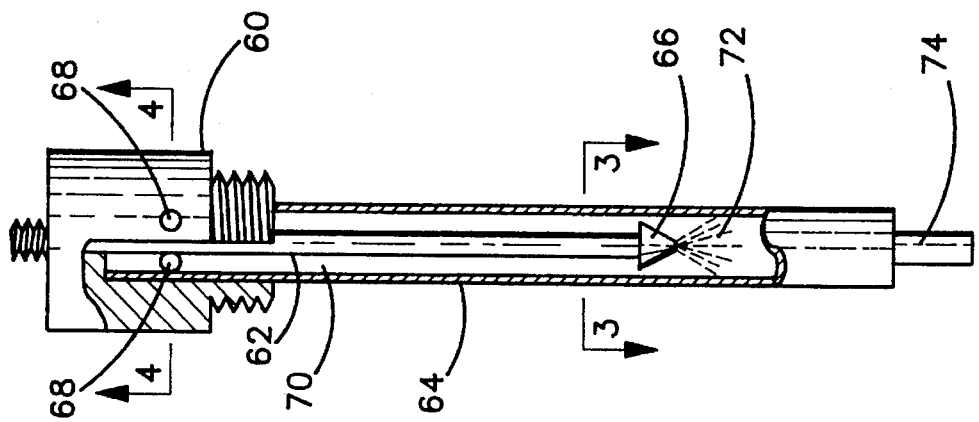
FIG. 2 is a cross-sectional planar view of the preferred eductor of the present invention.

The eductor means suitable for use in the present invention utilizes a high pressure jet of liquid to create a partial vacuum at an intake opening to draw in another fluid (air in this figure). FIGS. 2 and 3 hereof depict the eductor means of the present invention. For example, the eductor means is disposed in the stripping zone and is sealingly attached at bulkhead 60. A smaller diameter driver tubular member 62 is provided within a larger tailpipe member 64. As a liquid, preferably a recycle stream, is driven at relatively high pressures through the driver tubular member 62, a partial vacuum is created at a point above outlet nozzle 66 which is preferably stabilized against excessive vibration by being in contact with the inner wall of tailpipe member 64 at 3 or more points, more preferably at 3 or 4 points. While outlet nozzle 66 is shown in FIG. 2 hereof as being triangular in shape, it is understood that other shapes may also be used as long as they do not interfere with the intended function of the nozzle. Preferred shapes are those having relatively smooth or rounded, surfaces to enhance the flow of stripping gas. This partial vacuum draws air through inlet 68 and through the annular space 70 which is formed between the driver tubular member and the internal wall of the tailpipe member. The air becomes entrained in the spray of fine droplets 72 where mixing is thorough. The drive stream, with air entrained therein, is compressed at the end of the tailpipe member because the inside diameter (I.D.) of outlet tubular member 74 is smaller than the I.D. of the tailpipe 64. This compression assures that a greater amount of the air becomes entrained as fine bubbles within the droplets of the driver liquid. As the stream exits the tailpipe member at the bottom of the stripping zone, any excess air beyond the solubility limits of air in the driver liquid, plus dissolved air, is released in the form of "micro-fine" bubbles due to pressure drop at the exit of the tailpipe member. It is preferred that the length of outlet tubular member 74 be from about 3 to 12 inches, more preferably from about 4 to 8 inches, and most preferably from about 5.5 to 6.5 inches. The preferred distance from the outlet nozzle 66 to the bottom end of tailpipe member 64 is about 5 to 7 inches, preferably about 6 inches. It is also preferred that the I.D. of outlet tubular member 74 be from about ¼ to ¾, preferably about ½ the I.D. of tailpipe member 64. Also preferred is that the outside diameter (O.D.) be no more than about ½ the I.D. of tailpipe member 64. It is preferred that the I.D. of driver tubular member 62 be substantially equal to the I.D. of outlet tubular member 74.

While the eductor means are shown in FIG. 1 as being substantially vertically disposed in each stripping zone, it is to be understood that any configuration may be used as long as the eductors deliver the micro-fine bubbles to effect substantial removal of contaminants. That is, wherein at least about 80 wt. % of all organic contaminants are removed, preferably at least about 90 wt. %.

Returning again to FIG. 1, the micro-fine bubbles, which contain stripped contaminants, are released in the headspace between $L_T$ and $L_B$ which is defined by the level of the liquid in the process unit 1 and the top of the process unit. A blower means 4 is provided at the tail zone $Z_5$ to provide a sweep gas, preferably air, within the headspace. The contaminant-containing air, and the sweep air, are vented via line 15 positioned in the headspace above the first stripping zone $Z_1$. The blower 4 can also be used to "suck" the contaminant-containing air out of the process unit 1.

The eductor means $E_1$ to $E_4$ are operatively connected to manifold M for distribution of recycle liquid from zone $Z_5$ via recycle pump P. It is within the scope of the present invention that the recycle stream be heated, preferably by use of waste heat from the plant or refinery in which the contaminated aqueous steam is found, at some point between the recycle pump P and the eductor means $E_1$ to $E_4$. A conventional heat exchanger 16 may also be used in the line 17 between the recycle pump P and the manifold M. This of course will aid in the stripping capacity for a given amount of air. Also, it is preferred that the recycle stream not be heated above its boiling point.

While only one particular embodiment of the present invention has been shown and described, it is apparent that changes and modifications may be made without departing from this invention in its broader aspects. Therefore, the aim in the appended claims is to cover all such changes and modifications which fall within the true spirit and scope of this invention.

What we claim is:

1. A process for stripping organic contaminants from an organic contaminants-containing aqueous stream in a process unit having serially connected stripping zones, a tail stripping zone, and a continuous headspace communicating between said stripping zones, said process comprising:

(a) introducing said organic contaminants-containing aqueous stream into a bottom section of a first stripping zone in a manner to direct said stream toward a top section of said first stripping zone;

(b) introducing a micro-fine bubbles of a stripping gas into said bottom section of said first stripping zone by use of one or more eductors in a manner to contact and strip from said organic contaminants-containing aqueous stream at least a portion of said organic contaminants as said organic contaminants-containing aqueous stream flows toward said top section of said first stripping zone, each of said one or more eductors being comprised of a first and second substantially uniform diameter tubular member, each of said tubular members having an inlet end and an outlet end, and each being co-axial to each other, said first tubular member having a smaller diameter than said second tubular member wherein said outlet end of said first tubular member extends into said second tubular member to a predetermined distance short of said outlet end of said second tubular member, said outlet end of said first tubular member having attached thereto a discharge nozzle, said outlet end of said second tubular member having an axially disposed orifice of substantially smaller diameter than the diameter of said second tubular member, wherein said first tubular member is in fluid communication with a multi-stripped aqueous stream which flows into said first tubular member and exits therefrom through said discharge nozzle in the form of droplets, thereby causing said stripping gas to be drawn into said second tubular member which is in fluid communication with a source of said stripping gas, said stripping gas being entrained as fine bubbles in said droplets and exiting said second tubular member at said orifice as said micro-fine bubbles;

(c) flowing the once stripped organic contaminants-containing stream from said first stripping zone to a top section of an adjacent serially connected stripping zone;

(d) flowing said once stripped organic contaminants-containing stream from said top section of said adjacent stripping zone to a bottom section of said adjacent stripping zone;

(e) introducing additional micro-fine bubbles of said stripping gas into said bottom section of said adjacent stripping zone in a manner to contact and strip from said once stripped organic contaminants-containing aqueous stream at least another portion of said organic contaminants;

(f) continuing the process steps of (d) and (e) in each of said serially connected stripping zones to form said multi-stripped aqueous stream;

(g) flowing said multi-stripped aqueous stream into said tail stripping zone; and (h) removing said multi-stripped aqueous stream from said tail stripping zone.

2. The process according to claim 1 wherein said headspace extends above said organic contaminant-containing aqueous stream in each stripping zone and said tail stripping zone, and wherein in said headspace above said first stripping zone is a gas exit port, which further comprises introducing a sweep gas into said air space at a position above said tail stripping zone to move any gases accumulating above said stripping zones through said gas exit port.

3. The process according to claim 2 wherein at least a portion of said multi-stripped aqueous stream removed from said tail stripping zone is recycled to said stripping zones through said eductors.

4. The process according to claim 2 wherein said sweep gas is air.

5. A process for stripping organic contaminants from an organic contaminants-containing aqueous stream having no more than about 0.5 wt. percent of organics in a process unit having serially connected stripping zones, a tail stripping zone, and a continuous headspace communicating between said stripping zones, said process comprising:

(a) introducing said organic contaminants-containing aqueous stream into a bottom section of a first stripping zone in a manner to direct said stream toward a top section of said first stripping zone;

(b) introducing micro-fine stripping gas bubbles of a gas selected from the group consisting of air, carbon dioxide, nitrogen, methane, or combinations thereof, into said bottom section of said first stripping zone by use of one or more eductors in a manner to contact and strip from said organic contaminants-containing aqueous stream at least a portion of said organic contaminants as said organic contaminants-containing aqueous stream flows toward said top section of said first stripping zone; each of said one or more eductors being comprised of a first and second substantially uniform diameter tubular member, each of said tubular members having an inlet end and an outlet end, and each being co-axial to each other, said first tubular member having a smaller diameter than said second tubular member wherein said outlet end of said first tubular member extends into said second tubular member to a predetermined distance short of said outlet end of said second tubular member, said outlet end of said first tubular member having attached thereto a discharge nozzle, said outlet end of said second tubular member having an axially disposed orifice of substantially smaller diameter that the diameter of said second tubular member, wherein said first tubular member is in fluid communication with a multi-stripped aqueous stream which flows into said first tubular member and exits therefrom through said discharge nozzle in the form of droplets, thereby causing said stripping gas to be drawn into said second tubular member which is in fluid communication with a source of said stripping gas, said stripping gas being entrained as fine bubbles in said droplets and exiting said second tubular member at said orifice as said micro-fine bubbles;

(c) flowing the once stripped organic contaminants-containing stream from said first stripping zone to a top section of an adjacent serially connected stripping zone;

(d) flowing said once stripped organic contaminants-containing stream from said top section of said adjacent stripping zone to a bottom section of said adjacent stripping zone;

(e) introducing additional micro-fine stripping gas bubbles into said bottom section of said adjacent stripping zone in a manner to contact and strip from said once stripped organic contaminants-containing aqueous stream at least another portion of said organic contaminants;

(f) continuing the process steps of (d) and (e) in each of said serially connected stripping zones to form said multi-stripped aqueous stream;

(g) flowing said multi-stripped aqueous stream into said tail stripping zone; and (h) removing said multi-stripped aqueous stream from said tail stripping zone.

6. The process according to claim 5 wherein said headspace extends above said organic contaminant-containing aqueous stream in each stripping zone and said tail stripping zone, and wherein in said headspace above said first stripping zone is a gas exit port, which further comprises introducing a sweep gas into said air space at a position above said tail stripping zone to move any gases accumulating above said stripping zones through said gas exit port.

7. The process according to claim 6 wherein said multi-stripped aqueous stream removed from said tail stripping zone is recycled to a plurality of other said stripping zones through said eductors.

8. The process according to claim 6 wherein said sweep gas is air.

9. A process for stripping organic contaminants from an organic contaminants-containing aqueous stream in a process unit having serially connected stripping zones and a tail stripping zone, which comprises:

(a) introducing said organic contaminants-containing aqueous stream into a bottom section of a first stripping zone in a manner to direct said stream toward a top section of said first stripping zone;

(b) introducing micro-fine bubbles of a stripping gas into said bottom section of said first stripping zone by use of one or more eductors in a manner to contact and strip from said organic contaminants-containing aqueous stream at least a portion of said organic contaminants as said organic contaminants-containing aqueous stream flows toward said top section of said first stripping zone; each of said one or more eductors being comprised of a first and second substantially uniform diameter tubular member, each of said tubular members having an inlet end and an outlet end, and each being co-axial to each other, said first tubular member having a smaller diameter than said second tubular member wherein said outlet end of said first tubular member extends into said second tubular member to a predetermined distance short of said outlet end of said second tubular member, said outlet end of said first tubular member having attached thereto a discharge nozzle, said outlet end of said second tubular member having an axially disposed orifice of substantially smaller diameter than the diameter of said second tubular member, wherein said first tubular member is in fluid communication with a multi-stripped aqueous stream which flows into said first tubular member and exits therefrom through said discharge nozzle in the form of droplets, thereby causing said stripping gas to be drawn into said second tubular member which is in fluid communication with a source of said stripping gas, said stripping gas being entrained as fine bubbles in said droplets and exiting said second tubular member at said orifice as said micro-fine bubbles;

(c) flowing the once stripped organic contaminants-containing stream from said first stripping zone to a top section of an adjacent serially connected stripping zone;

(d) flowing said once stripped organic contaminants-containing stream from said top section of said adjacent stripping zone to a bottom section of said adjacent stripping zone;

(e) introducing additional micro-fine bubbles of said stripping gas into said bottom section of said adjacent stripping zone in a manner to contact and strip from said once stripped organic contaminants-containing aqueous stream at least another portion of said organic contaminants;

(f) continuing the process steps of (d) and (e) in each of said serially connected stripping zones to form said multi-stripped aqueous stream;

(g) flowing said multi-stripped aqueous stream into said tail stripping zone;

(h) removing said multi-stripped aqueous stream from said tail stripping zone; and (i) introducing a sweep gas into a headspace at a position above said tail stripping zone to move any gases accumulating above said stripping zones through a gas exit port above said first stripping zone, wherein said headspace is within said process unit and positioned above said organic contaminant-containing aqueous stream in each stripping zone and said tail stripping zone.

10. The process according to claim 9 wherein said multi-stripped aqueous stream removed from said tail stripping zone is recycled to a plurality of other said stripping zones through said eductors.

* * * * *